United States Patent
Mali et al.

(10) Patent No.: US 11,333,610 B2
(45) Date of Patent: May 17, 2022

(54) PERCARBOXYLIC ACID CONCENTRATION DETERMINATION TOOL AND INDICATOR SOLUTION USED IN PREPARING SAME

(71) Applicant: SARAYA CO., LTD., Osaka (JP)

(72) Inventors: Madan Mali, Kashiwara (JP); Satomi Sakai, Kashiwara (JP); Emiko Kawamukai, Kashiwara (JP)

(73) Assignee: SARAYA CO., LTD., Osaka (JP)

( * ) Notice: Subject to any disclaimer, the term of this patent is extended or adjusted under 35 U.S.C. 154(b) by 211 days.

(21) Appl. No.: 16/486,045

(22) PCT Filed: Feb. 14, 2018

(86) PCT No.: PCT/JP2018/005124
§ 371 (c)(1),
(2) Date: Aug. 14, 2019

(87) PCT Pub. No.: WO2018/151169
PCT Pub. Date: Aug. 23, 2018

(65) Prior Publication Data
US 2020/0049630 A1    Feb. 13, 2020

(30) Foreign Application Priority Data
Feb. 14, 2017    (JP) .............................. JP2017-024598

(51) Int. Cl.
*G01N 21/78* (2006.01)
*A61L 2/18* (2006.01)
*G01N 31/22* (2006.01)

(52) U.S. Cl.
CPC .............. *G01N 21/78* (2013.01); *A61L 2/186* (2013.01); *G01N 31/22* (2013.01)

(58) Field of Classification Search
CPC ...... G01N 21/78; G01N 31/22; G01N 31/228; G01N 31/00; A61L 2/186
See application file for complete search history.

(56) References Cited

U.S. PATENT DOCUMENTS

| 4,900,682 A | 2/1990 | Fischer et al. |
| 5,482,684 A | 1/1996 | Martens et al. |

(Continued)

FOREIGN PATENT DOCUMENTS

| CN | 2104445 U | 5/1992 |
| CN | 1111015 A | 11/1995 |

(Continued)

OTHER PUBLICATIONS

Maeda, "Simple demonstration experiment using oxidation-reduction reaction," *Chemical Education*, 59(1): 24-25 (2011).

(Continued)

*Primary Examiner* — Jennifer Wecker
*Assistant Examiner* — Oyeleye Alexander Alabi
(74) *Attorney, Agent, or Firm* — Leydig, Voit & Mayer, Ltd.

(57) ABSTRACT

The invention provides a percarboxylic acid concentration-determining device capable of determining the concentration of percarboxylic acid contained in an aqueous solution for chemical sterilization or disinfection that contains a percarboxylic acid as an active ingredient; and an indicator solution for use in preparing the device. The indicator solution contains a starch, an iodide, a thiosulfate, a water-soluble organic solvent, and water, with the starch, the iodide, the thiosulfate, and the water-soluble organic solvent being present in the following proportions, based on the total amount taken as 100 mass %: (a) starch: 0.01 to 5 mass %; (b) iodide: 0.01 to 5 mass %; (c) thiosulfate: 0.01 to 10 mass %; and (d) water-soluble organic solvent: 0.1 to 40 mass %, wherein the total amount of (a), (b), and (c) is greater than 0.6 mass %.

20 Claims, 2 Drawing Sheets

(56) References Cited

U.S. PATENT DOCUMENTS

| | | |
|---|---|---|
| 5,603,897 A | 2/1997 | Heller et al. |
| 5,906,916 A | 5/1999 | Wu |
| 2003/0194346 A1 | 10/2003 | Read |
| 2006/0045796 A1 | 3/2006 | Anderle et al. |
| 2007/0003995 A1 | 1/2007 | Song et al. |
| 2007/0054412 A1 | 3/2007 | Cregger et al. |
| 2007/0134797 A1 | 6/2007 | Read |
| 2008/0009641 A1* | 1/2008 | Miyazaki ............ C07C 409/24 549/486 |
| 2009/0047176 A1* | 2/2009 | Cregger ............ A61L 2/28 422/28 |
| 2009/0325308 A1 | 12/2009 | Harada |
| 2010/0124784 A1 | 5/2010 | Read |
| 2010/0136705 A1 | 6/2010 | Kojima et al. |
| 2010/0227000 A1 | 9/2010 | Ames et al. |
| 2011/0206554 A1 | 8/2011 | Anderle et al. |
| 2011/0206556 A1 | 8/2011 | Harada |
| 2012/0149094 A1 | 6/2012 | Smith et al. |
| 2013/0119265 A1 | 5/2013 | Anderle et al. |

FOREIGN PATENT DOCUMENTS

| | | |
|---|---|---|
| CN | 1151121 A | 6/1997 |
| CN | 1610561 A | 4/2005 |
| CN | 101065154 A | 10/2007 |
| CN | 101095961 A | 1/2008 |
| CN | 101395464 A | 3/2009 |
| CN | 102413846 A | 4/2012 |
| CN | 102706872 A | 10/2012 |
| CN | 103439322 A | 12/2013 |
| EP | 0916946 A3 | 6/2001 |
| JP | 2005-514112 A | 5/2005 |
| JP | 2005-350613 A | 12/2005 |
| JP | 2008-014685 A | 1/2008 |
| JP | 2014-114227 A | 6/2014 |
| WO | WO 2003/057262 A1 | 7/2003 |
| WO | WO 2008/133321 A1 | 11/2008 |

OTHER PUBLICATIONS

Saraya Co., Ltd., "Acecide 6% disinfectant product information (53-0115-00-4PDF)" [obtained at http://med.saraya.com/products/acecide/ on Mar. 19, 2019].

Japanese Patent Office, International Search Report in International Patent Application No. PCT/JP2018/005124 (dated May 15, 2018).

* cited by examiner

PERCARBOXYLIC ACID CONCENTRATION DETERMINATION TOOL AND INDICATOR SOLUTION USED IN PREPARING SAME

CROSS-REFERENCE TO RELATED APPLICATIONS

This patent application is the U.S. national phase of International Patent Application No. PCT/JP2018/005124, filed Feb. 14, 2018, which claims the benefit of Japanese Patent Application No. 2017-024598, filed Feb. 14, 2017, which are incorporated by reference in their entireties herein.

TECHNICAL FIELD

The present invention relates to a device for use in determining the concentration of percarboxylic acid in a test sample, and to an indicator solution for use in preparing the device. More particularly, the present invention relates to a device for use in easily and sensitively determining the concentration of percarboxylic acid, which is an active ingredient of an aqueous solution for chemical sterilization or disinfection (which hereinafter may be simply referred to as a "PCAC-determining device"; here, the term "PCAC" is an abbreviation for percarboxylic acid concentration), and to an indicator solution for use in preparing the device.

The present invention also relates to use of the PCAC-determining device. More particularly, the present invention relates to a method for determining whether an aqueous solution for chemical sterilization or disinfection contains a percarboxylic acid in an amount effective for sterilization or disinfection, using the PCAC-determining device.

BACKGROUND ART

Percarboxylic acids, i.e., peroxides of carboxylic acids, have a broad microbicidal spectrum: they kill not only viruses, bacteria, and fungi, but also highly resistant acid-fast bacteria and bacterial spores. Among these, peracetic acid is an active ingredient of chemical sterilants or disinfectants widely used in the food and medical fields, where high safety is required, because its decomposition products are acetic acid and water. In particular, in the food field, peracetic acid is used for aseptic filling of PET bottles and paper containers in, for example, beverage filling plants. Peracetic acid is also used as a liquid chemical sterilant or a disinfectant in the medical field to disinfect medical instruments, equipment, or devices that are reused, such as endoscopes.

Peracetic acid is generally provided in the form of an equilibrium mixture with acetic acid and hydrogen peroxide, and is used at a predetermined concentration by dilution with water before use. When doing so, it is necessary to adjust the concentration to an appropriate level in order to effectively exhibit microbicidal efficacy. As a method of controlling such an appropriate concentration, there is a method of measuring the concentration using an electrochemical sensor. In particular, in food factories, which continuously use a large amount of peracetic acid solution, the peracetic acid solution can be adjusted and controlled at an appropriate concentration without requiring human operations by introducing such sensors in-line. However, the installation costs are high, and the sensors cannot be used at a location other than where they are installed.

In disinfectants used in the medical field, peracetic acid is often combined with a buffering agent and a stabilizing agent. In addition, organic matter, such as blood on a medical instrument to be disinfected, is mixed into such disinfectants. Because of these interferences, the peracetic acid concentration cannot be accurately determined with an electrochemical sensor. In the medical field, since disinfectants are usually reused (repeatedly used), it is highly necessary to confirm, at the time of use, that the concentration is an effective concentration at which microbicidal efficacy is exhibited (effective microbicidal concentration). For example, peracetic acid is currently required to be used at 2000 ppm (0.20 mass %) or more in Japan. In particular, the influence of temperature or ultraviolet rays, and the presence of water, organic matter, etc. promotes a decrease in the peracetic acid concentration, and sometimes the concentration decreases for several minutes. Thus, sensitivity (accuracy) high enough to confirm a difference of about 100 ppm (0.01 mass %) to 200 ppm (0.02 mass %) is required. In medical settings, since healthcare workers often confirm the effectiveness of a disinfectant periodically, it is also required that the work can be easily carried out as routine work.

The Peracetic Acid Counter PA-300 (Hiranuma Sangyo Co., Ltd., Japan) and Peracetic Acid and Hydrogen Peroxide Analyzer (Ricoh Kyosan Co., Ltd., Japan) are sold as devices for automatically performing an electrochemical titration operation to measure the concentration of peracetic acid. These devices enable a wide range of peracetic acid concentrations to be quantified by changing reagents and the sampling amount. However, these devices are problematic in that they require introduction of an expensive device or an operation using multiple reagents.

Liquid determination kits, such as Pac Test (registered trademark) (Kyoritsu Chemical-Check Lab., Corp., Japan), or test strips that are used in such a manner that they are immersed in a disinfecting liquid to be measured for checking a color change between before and after immersion, such as Acecide (registered trademark) checker (Saraya Co., Ltd., Japan), can be more easily handled (Non-patent Literature 1). Such a test strip uses an iodine-starch reaction in which a peroxide of an organic carboxylic acid (which hereinafter may be simply referred to as a "percarboxylic acid"), such as peracetic acid, iodide ion, and starch are reacted to produce a blue complex. This is advantageous in that the cost is low, whether the concentration of peracetic acid in a disinfecting liquid is equal to or greater than the effective microbicidal concentration can be (qualitatively) determined in a short period of time at the site when necessary, and the concentration of peracetic acid can be semi-quantitatively determined by comparing with colors of the color scale. However, since the determination is made visually by a person, it is inevitable that the determination varies when the presentation result (color) of a test strip is compared with the color scale. Obtaining high measurement accuracy is thus not easy.

As prior art concerning such a test strip for determining the concentration of peracetic acid, for example, Patent Literature 1 discloses, as a concentration-determining device for a percarboxylic acid solution containing peracetic acid, a test strip in which filter paper is impregnated with an indicator solution containing an iodide and a chromogen. Patent Literature 1 discloses that the concentration of peracetic acid in a disinfecting liquid containing peracetic acid is determined using as an index a color change from yellow to yellowish brown caused by immersing the test strip in the disinfecting liquid. Patent Literature 2 discloses that a solution containing an iodide, a buffer, and a water-soluble polymer (preferably using a cellulosic polymer as a visible color developing agent) is used for preparing a test strip. The test strips according to these Patent Literature instances produce a continuous color change and thus require color samples that show correlation between the color depth of the test strips and the concentration of peracetic acid. The distinguishable concentration difference is 500 ppm (0.05 mass %). The determination can be made over a wide concentration range; however, since the color changes while exhibiting an intermediate color, the desired peracetic acid concentration cannot be clearly and sensitively estimated.

As prior art concerning a test strip for determining the concentration of peracetic acid, for example, Patent Literature 3 can be mentioned. The test strip of Patent Literature 3 is prepared by impregnating filter paper with an indicator solution containing potassium iodide, thiosulfate ion, starch, and water (the mass ratio of potassium iodide and thiosulfate ion being 0.7 to 0.3) and drying the solution. The test strip uses a mechanism that when the test strip is immersed in a disinfectant containing a percarboxylic acid, such as peracetic acid, the iodide ion of the test strip react with the percarboxylic acid to produce iodine, and the iodine is bonded to the starch (an iodine-starch reaction), thereby exhibiting a color from blue to deep purple. The Examples of Patent Literature 3 indicate that for a percarboxylic acid in an amount of 27 mM or more, the test strip enables determination of peroxide concentrations of 27 mM and 40 mM, which respectively correspond to peracetic acid concentrations of 2000 ppm (0.2 mass %) and 3000 ppm (0.3 mass %). Thus, a peracetic acid concentration difference of 1000 ppm (0.1 mass %) can be determined. This test strip is advantageous in that color stability in the reaction area can be maintained for several tens of seconds or more. However, multiple colors, i.e., brown, blue, and deep purple, are shown at the time of determination for the test strip, and variations in determination are thus likely to be caused. From this viewpoint, it is also difficult to determine a peracetic acid concentration difference of 100 ppm (0.01 mass %) to 200 ppm (0.02 mass %).

In order to prevent hospital-associated infection, it is necessary to appropriately and strictly perform disinfection management of medical instruments etc. In particular, when the concentration of percarboxylic acid, such as peracetic acid, which is an active ingredient, is determined to be positive (equal to or greater than the effective concentration) even though the concentration is actually lower than the effective amount, there is a high risk that the microbicidal effect is insufficient. Thus, determination of the peracetic acid concentration in a practical solution of the disinfectant described above is very important. On the other hand, it is also required that the determination be a simple operation so that healthcare workers can perform the determination as a routine in everyday work, and that the determination be performed with fewer errors (false negatives and false positives) and with high accuracy. Moreover, it is desirable that the determination can be preferably performed visually without the use of an expensive and complicated device.

CITATION LIST

Patent Literature

PTL 1: U.S. Pat. No. 4,900,682
PTL 2: U.S. Pat. No. 5,906,916
PTL 3: JP2008-014685A

Non-Patent Literature

NPL 1: Saraya Co., Ltd., Acecide 6% disinfectant product information (53-0115-00-4PDF) http://med.saraya.com/products/acecide/ (Medical SARAYA, website of Saraya Co., Ltd., for healthcare professionals)

SUMMARY OF INVENTION

Technical Problem

The present invention has been developed to solve the above problems. An object of the present invention is to provide a device for use in determining whether the concentration of percarboxylic acid contained in an aqueous solution for chemical sterilization or disinfection that contains a percarboxylic acid, such as peracetic acid, as an active ingredient (which hereinafter may be collectively referred to as an "aqueous solution for disinfection") is equal to or greater than a concentration effective for chemical sterilization, microbicide, or disinfection (an effective microbicidal concentration) (a PCAC-determining device); and to provide an indicator solution for use in preparing the device. In particular, an object of the present invention is to provide a device that enables easily determining whether the aqueous solution for disinfection contains the percarboxylic acid at an effective microbicidal concentration, with high accuracy and with low risk of incorrect determination (a PCAC-determining device); and to provide an indicator solution for preparing the device.

Further, another object of the present invention is to provide a method for determining whether an aqueous solution for disinfection contains a percarboxylic acid at a concentration effective for chemical sterilization, microbicide, or disinfection, using the PCAC-determining device.

Solution to Problem

The present inventors conducted extensive research to achieve the above objects, and found that the color developed with respect to an peroxycarboxylic acid at the determination part of a PCAC-determining device becomes sharp, and clearness is improved, by preparing an indicator solution to be impregnated into the determination part of the PCAC-determining device by using a water-soluble organic solvent, such as a lower alcohol, in addition to water conventionally used as a solvent. More specifically, conventional indicator solutions, which use only water as a solvent, have a problem in that if such a solution is impregnated into the determination part and kept dry, the color developed by a reaction with a percarboxylic acid is bluish black (deep blue to deep purple), and in that color unevenness (white spotting) occurring when the percarboxylic acid concentration is less than the effective microbicidal concentration is difficult to recognize (indistinctness). The inventors found that, in contrast, when an indicator solution containing water and a water-soluble organic solvent, such as a lower alcohol, in combination as solvents is used, black that does not contain a bluish color (pure black) can be developed, which makes contrast with white clear, and that the occurrence of the color unevenness (white spotting) can be thus recognized clearly with high accuracy (without incorrect recognition).

The present invention has been accomplished based on the above findings and includes the following embodiments.
(I) Indicator Solution for Preparing PCAC-Determining Device
(I-1) An indicator solution comprising a starch, an iodide, a thiosulfate, a water-soluble organic solvent, and water,
the starch, the iodide, the thiosulfate, and the water-soluble organic solvent being present in the following proportions, based on the indicator solution taken as 100 mass %:

(a) starch: 0.01 to 5 mass %;
(b) iodide: 0.01 to 5 mass %;
(c) thiosulfate: 0.01 to 10 mass %; and
(d) water-soluble organic solvent: 0.1 to 40 mass %,
wherein the total amount of (a), (b), and (c) is greater than 0.6 mass %.

(I-2) The indicator solution according to (I-1), wherein (d) the water-soluble organic solvent is at least one member selected from the group consisting of $C_{1-6}$ lower alcohols, polyhydric alcohols, acetone, and acetonitrile, preferably at least one member selected from the group consisting of ethanol, methanol, isopropyl alcohol, propylene glycol, glycerol, acetone, and acetonitrile.

(I-3) The indicator solution according to (I-1), wherein (d) the water-soluble organic solvent is a $C_{1-6}$ lower alcohol, and the proportion of the organic solvent is 0.5 mass % or more based on the indicator solution taken as 100 mass %.

(I-4) The indicator solution according to any one of (I-1) to (I-3), wherein the iodide is at least one member selected from the group consisting of sodium iodide, potassium iodide, and ammonium iodide, preferably potassium iodide.

(I-5) The indicator solution according to any one of (I-1) to (I-4), wherein the thiosulfate is at least one member selected from the group consisting of sodium thiosulfate, potassium thiosulfate, ammonium thiosulfate, and hydrates thereof, preferably sodium thiosulfate pentahydrate.

(I-6) The indicator solution according to any one of (I-1) to (I-5), for use in preparing a device for use in determining whether the concentration of percarboxylic acid in an aqueous solution for chemical sterilization or disinfection that contains a percarboxylic acid is a concentration effective for chemical sterilization or disinfection (a PCAC-determining device).

(I-7) The indicator solution according to (I-6), wherein the PCAC-determining device comprises a part for determining the concentration of percarboxylic acid in an aqueous solution for chemical sterilization or disinfection (a determination part), and (a) the starch, (b) the iodide, and (c) the thiosulfate are contained at the determination part in a total amount (dry weight) of greater than 0.24 mg/cm² ((a)+(b)+(c)>0.24 mg/cm²).

(I-8) The indicator solution according to (I-7), wherein the PCAC-determining device has the following characteristic:

$$A/B<2.5$$

$$A/C<2.0 \quad (4)$$

A: a threshold (mass %) of an effective concentration of percarboxylic acid contained in an aqueous solution for chemical sterilization or disinfection to be measured,
B: a dry weight (mg/cm²) of iodide ion contained in the determination part of the PCAC-determining device,
C: a dry weight (mg/cm²) of thiosulfate ion contained in the determination part of the PCAC-determining device.

(I-9) The indicator solution according to (I-6) to (I-8), wherein the percarboxylic acid, which is a target of the PCAC-determining device, is a peroxide of a $C_{1-8}$ organic carboxylic acid.

(II) PCAC-Determining Device
(II-1) A PCAC-determining device comprising at least a part for determining the concentration of percarboxylic acid (a determination part), wherein a member that forms the determination part comprises the indicator solution according to any one of (I-1) to (I-9) in a dry state.
(II-2) The PCAC-determining device according to (II-1), which has the following characteristics (1) to (3):

(1) the device is a device for determining whether the concentration of percarboxylic acid in an aqueous solution for chemical sterilization or disinfection that contains a percarboxylic acid is a concentration effective for sterilization or disinfection;
(2) the device comprises at least a part for determining the concentration of percarboxylic acid in an aqueous solution for chemical sterilization or disinfection (a determination part); and
(3) the member that forms the determination part comprises (a) the starch, (b) the iodide, and (c) the thiosulfate in a total amount of greater than 0.24 mg/cm² on a dry weight basis.

(II-3) The PCAC-determining device according to (II-2), which further has the following characteristic (4):

$$A/B<2.5$$

$$A/C<2.0 \quad (4)$$

A: a threshold (mass %) of an effective concentration of percarboxylic acid contained in an aqueous solution for chemical sterilization or disinfection to be measured,
B: a dry weight (mg/cm²) of iodide ion contained in the determination part of the PCAC-determining device,
C: a dry weight (mg/cm²) of thiosulfate ion contained in the determination part of the PCAC-determining device.

(II-4) The PCAC-determining device according to (II-2) or (II-3), wherein the aqueous solution for chemical sterilization or disinfection comprises a percarboxylic acid in an amount of 0.01 to 1 mass %, preferably 0.03 to 0.5 mass %, and more preferably 0.05 to 0.4 mass %.

(II-5) The PCAC-determining device according to any one of (II-1) to (II-4), wherein the percarboxylic acid, which is a target in the determination, is a peroxide of a $C_{1-8}$ organic carboxylic acid.

(III) PCAC-Determining Kit
(III-1) A PCAC-determining kit for use in determining a percarboxylic acid concentration in a test sample, comprising the PCAC-determining device according to any one of (II-1) to (II-5).

(IV) Method of Producing PCAC-Determining Device
(IV-1) A method for producing the PCAC-determining device according to any one of (II-1) to (II-5), the method comprising:

(i) impregnating the indicator solution according to any one of (I-1) to (I-9) into a member that forms a part for determining the concentration of percarboxylic acid in an aqueous solution for chemical sterilization or disinfection (a determination part); and
(ii) drying the member.

(IV-2) The method according to (IV-1), wherein the impregnation step is a step of impregnating the indicator solution into the member that forms the determination part so that (a) the starch, (b) the iodide, and (c) the thiosulfate are contained in a total amount of greater than 0.24 mg/cm² on a dry weight basis.

(IV-3) The method according (IV-2), which has the following characteristic:

$$A/B<2.5$$

$$A/C<2.0$$

A: a threshold (mass %) of an effective concentration of percarboxylic acid contained in an aqueous solution for chemical sterilization or disinfection to be measured,
B: a dry weight (mg/cm²) of iodide ion contained in the determination part of the PCAC-determining device, C: a dry weight (mg/cm$^2$) of thiosulfate ion contained in the determination part of the PCAC-determining device.

(V) Method for Determining Concentration of Percarboxylic Acid in Test Sample (V-1) A method for determining whether the concentration of percarboxylic acid in an aqueous solution for chemical sterilization or disinfection that contains a percarboxylic acid as an active ingredient is a concentration effective for chemical sterilization or disinfection, the method comprising:

allowing the aqueous solution for chemical sterilization or disinfection to come into contact with the determination part of the percarboxylic acid concentration-determining device according to any one of (II-1) to (II-5) to develop a color at the determination part.

(V-2) A method for determining whether the concentration of percarboxylic acid in an aqueous solution for chemical sterilization or disinfection that contains a percarboxylic acid as an active ingredient is a concentration effective for sterilization or disinfection, the method comprising:

(1) immersing at least the determination part of the PCAC-determining device according to any one of (II-1) to (II-5) in the aqueous solution for chemical sterilization or disinfection;

(2) observing color development at the determination part; and (3) determining whether the concentration of percarboxylic acid in the aqueous solution for chemical sterilization or disinfection is effective or ineffective for sterilization or disinfection, using a state of the color development at the determination part as an index.

Advantageous Effects of Invention

The PCAC-determining device prepared using the indicator solution of the present invention enables clear black to be developed by a reaction with a percarboxylic acid at a concentration equal to or greater than the effective microbicidal concentration in an aqueous solution for chemical sterilization or disinfection (an aqueous solution for disinfection). In contrast, in the case of a reaction with a percarboxylic acid at a concentration less than the effective microbicidal concentration, the reaction does not sufficiently take place (reaction failure), and white is shown or a phenomenon in which white spots are mixed in a black color developed by the reaction occurs (white spotting). The white spots can be clearly and sensitively distinguished as color unevenness by white and black contrast against the black background. Therefore, the PCAC-determining device of the present invention enables easy and accurate visual determination of whether an aqueous solution for disinfection contains a percarboxylic acid at a concentration effective for chemical sterilization or disinfection.

Figure 1:
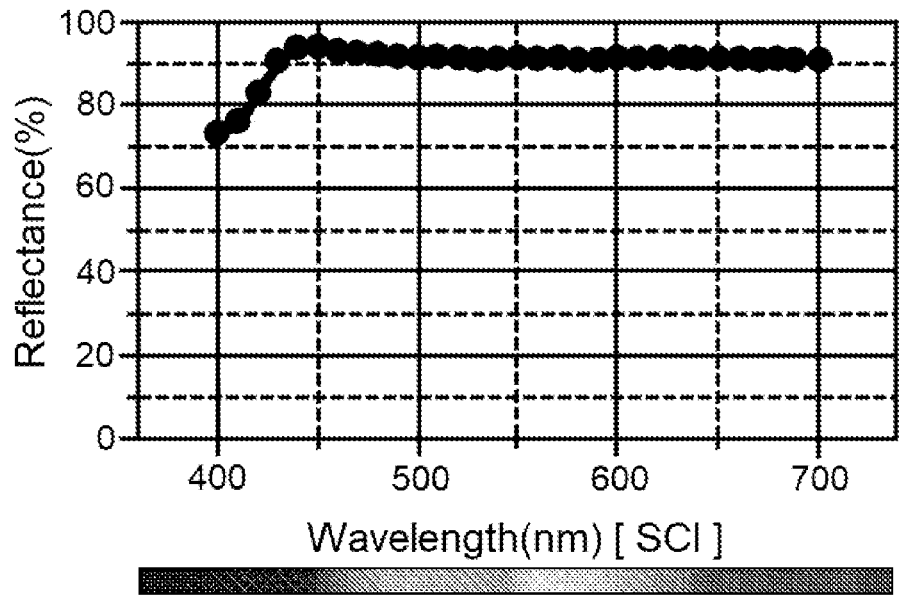
FIG. 1 shows results of reflectance (%) measured when filter paper constituting the determination part of a test strip was irradiated with light of wavelengths of 400 to 700 nm in Experimental Example 8.

DESCRIPTION OF EMBODIMENTS (I) Indicator Solution for Preparing PCAC-Determining Device The indicator solution of the present invention comprises a starch, an iodide, a thiosulfate, a water-soluble organic solvent, and water, and is used for preparing the PCAC-determining device of the present invention, described later. In this specification, this solution may be simply referred to as an "indicator solution."

The PCAC-determining device of the present invention is an auxiliary device used for determining the concentration of percarboxylic acid contained in a test sample using an iodine-starch reaction.

The term "iodine-starch reaction" as used herein generally refers to a reaction in which iodine and starch form a complex to develop a color. When a peracid (e.g., a percarboxylic acid) is present in the presence of an iodide (e.g., potassium iodide) and starch, iodide ion are converted to iodine due to its oxidation action, and the iodine reacts with the starch to develop a color. Thus, the reaction can be used in determining the presence or absence of a peracid (e.g., a percarboxylic acid) and its concentration based on the presence or absence of color and its degree. That is, the iodine-starch reaction can be used in determining whether an aqueous solution for disinfection containing a percarboxylic acid as an active ingredient contains the percarboxylic acid at an effective microbicidal concentration. Specifically, the minimum effective microbicidal concentration, which is the boundary between the effective microbicidal concentration and ineffective microbicidal concentration of percarboxylic acid, is used as a critical point (threshold); the concentrations of the iodide and starch in a reaction system, or the concentrations of one or more other components in addition to these concentrations, are set so that there is a difference in the degree and state of coloration between an iodine-starch reaction at a concentration equal to or greater than the threshold (effective microbicidal concentration) and an iodine-starch reaction at a concentration less than the threshold (ineffective microbicidal concentration); the reaction can be thus used for determining whether the concentration of percarboxylic acid in an aqueous solution for disinfection is an effective microbicidal concentration.

The color developed by an iodine-starch reaction is generally bluish purple. However, the indicator solution of the present invention is characterized in that the solution is obtained by dissolving an indicator containing an iodide and a starch in a solvent containing not only water but also a water-soluble organic solvent; thus, the color developed by an iodine-starch reaction is black, not bluish purple. Black is a color that allows a difference in shade (tone) of color (contrast with the color exhibited when the reaction does not take place (white)) to be clearly determined, compared with the conventional bluish purple. Thus, whether the concentration of percarboxylic acid contained in an aqueous solution for disinfection is a concentration effective for chemical sterilization or disinfection can be determined sensitively.

The components of the indicator solution for an iodine-starch reaction are described below.

(a) Starch

Starch is generally composed of 0 to 30% linear amylose, in which glucose units are joined through α-1,4 linkages, and 70 to 100% amylopectin, which has α-1,6-bond branches. The starch used in the present invention is not limited, and is preferably a water-soluble starch that is easily solubilized in water. Here, solubilization includes the case of dissolving while warming water. The source of the starch is not particularly limited as long as the starch has the above characteristics. Examples of the source of the starch include corn, potato, sweet potato, cassava, wheat, non-glutinous rice, and the like. These starches may be used singly or in a combination of two or more. Preferred examples include corn starch and potato starch. In addition to these common starches, starches obtained by subjecting a common starch to acid treatment, solubilizing it in water, and further decreasing the viscosity of the solution can be used. Such starches are commercially available as soluble starches. Soluble starches, which are easily soluble in water, can be suitably used in the present invention.

The proportion of the starch contained in the indicator solution (100 mass %) is not limited and is, for example, 0.01 mass % or more, preferably 0.2 mass % or more, and more preferably 0.23 mass % or more. The upper limit is not limited and is, for example, 5 mass % or less, preferably 4.5 mass % or less, and more preferably 4.36 mass % or less.

(b) Iodide

Any iodide that produces an iodine ion in the indicator solution can be used. Examples include alkali metal salts of iodine, such as potassium iodide and sodium iodide, and ammonium salts of iodine, such as ammonium iodide. These iodides may be used singly or in a combination of two or more. Potassium iodide is preferable. These iodides, including potassium iodide, are not particularly limited as long as they are commercially available for reagents or production.

The proportion of the iodide contained in the indicator solution (100 mass %) is not limited and is, for example, 0.01 mass % or more, preferably 0.1 mass % or more, and more preferably 0.13 mass % or more. The upper limit is not limited and is, for example, 5 mass % or less, preferably 3 mass % or less, and more preferably 2.96 mass % or less.

(c) Thiosulfate

Any thiosulfate that produces a thiosulfate ion in the indicator solution can be used. Examples include alkali metal salts of thiosulfuric acid, such as potassium thiosulfate and sodium thiosulfate, and ammonium salts of thiosulfuric acid, such as ammonium thiosulfate. These thiosulfates may be used singly or in a combination of two or more. Sodium thiosulfate and ammonium thiosulfate are preferable. These may be in the form of a hydrate. These thiosulfates, including sodium thiosulfate, are not particularly limited as long as they are commercially available for reagents or production.

The proportion of the thiosulfate contained in the indicator solution (100 mass %) is not particularly limited and is, for example, 0.01 mass % or more, and preferably 0.25 mass % or more. The upper limit is not limited and is, for example, 10 mass % or less, preferably 8 mass % or less, more preferably 6 mass % or less, and even more preferably 5.57 mass % or less.

(d) Water-Soluble Organic Solvent "Water-soluble organic solvent" means an organic solvent that is soluble in water. Specific examples include $C_{1-4}$ lower alcohols, such as methanol, ethanol, n-propyl alcohol, isopropyl alcohol, and t-butyl alcohol; polyhydric alcohols, such as ethylene glycol, propylene glycol, and glycerol; 1,2-dimethoxyethane, tetrahydrofuran (THF), 1,4-dioxane, acetone, acetonitrile, dimethylformamide (DMF), triethylamine, and the like. Preferred examples include methanol, ethanol, isopropyl alcohol, propylene glycol, glycerol, acetone, and acetonitrile. Ethanol, methanol, isopropyl alcohol, propylene glycol, glycerol, acetone, and acetonitrile are more preferable. These solvents may be used singly or in a combination of two or more. Preferred examples of the combination include, but are not limited to, a combination of glycerol and one or more other organic solvents, a combination of acetone and one or more other organic solvents, and a combination of acetonitrile and one or more other organic solvents. The other organic solvents are not particularly limited, and preferred examples include ethanol. As described later, use of such a combination of two or more organic solvents enables the effects of the present invention to be achieved with smaller amounts. These solvents are not particularly limited as long as they are commercially available for reagents or production.

The proportion of the water-soluble organic solvent contained in the indicator solution (100 mass %) is not limited as long as the effects of the present invention are achieved, and it can be suitably set from the range of 0.1 to 40 mass % depending on the type of organic solvent used.

When ethanol, for example, is used as a water-soluble organic solvent, the proportion of ethanol contained in the indicator solution (100 mass %) is not limited and is, for example, 0.4 mass % or more, preferably 0.5 mass % or more, and more preferably 0.6 mass % or more when used alone. The upper limit is not limited and is 40 mass % or less, preferably 30 mass % or less or 29.2 mass % or less, and more preferably 25 mass % or less. As described above, when ethanol is used in combination with one or more other organic solvents, it can be added in an amount smaller than the above amount, and the lower limit of the amount of ethanol is, for example, 0.05 mass % or more, and preferably 0.1 mass % or more.

As in the case of ethanol, when isopropanol, for example, is used as a water-soluble organic solvent, the proportion of isopropanol contained in the indicator solution (100 mass %) is not limited and is, for example, 0.4 mass % or more, preferably 0.5 mass % or more, and more preferably 0.6 mass % or more when used alone. The upper limit is not limited and is 40 mass % or less, preferably 30 mass % or less, and more preferably 25 mass % or less. When isopropanol is used in combination with one or more organic solvents, it can be added in an amount smaller than the above amount, and the lower limit of the amount of isopropanol is, for example, 0.05 mass % or more, and preferably 0.1 mass % or more.

When glycerol, for example, is used as a water-soluble organic solvent, the proportion of glycerol contained in the indicator solution (100 mass %) is not limited and is, for example, 0.1 mass % or more, preferably 0.4 mass % or more, and more preferably 0.5 mass % or more or 1 mass % or more. The upper limit is not limited and is 40 mass % or less, preferably 30 mass % or less, and more preferably 25 mass % or less.

When acetone, for example, is used as a water-soluble organic solvent, the proportion of acetone contained in the indicator solution (100 mass %) is not limited and is, for example, 0.1 mass % or more, preferably 0.2 mass % or more or 0.4 mass % or more, and more preferably 1 mass % or more. The upper limit is not limited and is 40 mass % or less, preferably 30 mass % or less, and more preferably 25 mass % or less.

As described later in Example 32 (a combination of acetone and glycerol), Example 33 (a combination of methanol, propylene glycol, and acetonitrile), Example 34 (a combination of ethanol and acetone), and Example 35 (a combination of ethanol and acetonitrile), use of a combination of two or more water-soluble organic solvents enables the effects of the present invention to be achieved while keeping the amount of each solvent low. Such enhancement of the effects of the present invention by use of a combination of water-soluble organic solvents is not limited to the combinations described above. The same applies to other water-soluble organic solvents.

(e) Water and Other Components

The indicator solution of the present invention comprises water in addition to (a) to (d) above. The water is not limited as long as it does not affect an iodine-starch reaction. For example, purified water, ion-exchanged water, distilled water, etc. can be used without any limitation as long as they have the above characteristics. The water is used as adjustment water so that the components (a) to (d) are contained in the amounts described above; therefore, the amount of water is not particularly limited and can be suitably set within the range of generally 60 to 99 mass %.

Other components, such as potassium chloride for adjusting ion concentration etc., and an antimicrobial agent for preventing deterioration due to microorganisms, may be further added to the indicator solution of the present invention.

(f) Preparation of Indicator Solution

The indicator solution of the present invention can be produced by mixing the components (a) to (e) in the proportions described above. Specifically, the indicator solution can be prepared by homogeneously dissolving the components (a) to (c) in (d) the water-soluble organic solvent and (e) the water used as solvents. In preparing the indicator solution, components that are poorly soluble in cold water and an organic solvent, such as (a) the starch, may be dissolved in pre-warmed water and then mixed with the organic solvent.

The proportions of (a) to (d) are as described above, and it is further preferred that the total amount of the component (a), the component (b), and the component (c) is greater than 0.6 mass %, preferably 0.7 mass % or more, and more preferably 1 mass % or more, based on the indicator solution taken as 100 mass %. The upper limit is, for example, 20 mass %, and preferably 15 mass % or less. The amounts of (b) the iodide and (c) the thiosulfate among these components are preferably set according to the following formula, in relation to the threshold of the effective microbicidal concentration of percarboxylic acid in an aqueous solution for disinfection, which is the target in the determination (the critical point of the effective concentration of percarboxylic acid in the aqueous solution for disinfection that exhibits a sterilization, microbicidal, or disinfection effect). The details are given in the following formula (II).

$$A/B < 2.5$$

$$A/C < 2.0$$

A: the threshold (mass %) of the effective concentration of percarboxylic acid contained in an aqueous solution for disinfection to be measured
B: the dry weight ($mg/cm^2$) of iodide ion contained in the determination part of a PCAC-determining device
C: the dry weight ($mg/cm^2$) of thiosulfate ion contained in the determination part of a PCAC-determining device The phrase "dry weight ($mg/cm^2$) of iodide ions contained in the determination part of a PCAC-determining device" or "dry weight ($mg/cm^2$) of thiosulfate ion contained in the determination part of a PCAC-determining device" means the amount ($mg/cm^2$) of a solute (iodide ion or thiosulfate ion) per unit area of the determination part of a PCAC-determining device prepared by impregnating the part with the indicator solution and drying the part. The amount of the solute per unit area of the determination part of the PCAC-determining device is determined by dividing the dry mass (mg) of the solute contained in the determination part of the PCAC-determining device by the area ($cm^2$) of the determination part.

The indicator solution of the present invention prepared in this manner is used for preparing the PCAC-determining device of the present invention, described later. Specifically, the indicator solution of the present invention is impregnated into the member of the determination part of the PCAC-determining device, dried, and used in a dry state. The concentration of percarboxylic acid contained in a test sample is determined based on the degree or state of color developed at the determination part of the PCAC-determining device by an iodine-starch reaction in the presence of the percarboxylic acid in the test sample. It is thus necessary for the indicator solution, with which the determination part is to be impregnated, to contain all of the components homogeneously dissolved in it.

The percarboxylic acid to be measured in the present invention is described later.

(II) Percarboxylic Acid Concentration-Determining Device (PCAC-Determining Device) and Kit Comprising the Device The PCAC-determining device (which hereinafter may be simply referred to as a "device") of the present invention is a device used for determining whether the concentration of percarboxylic acid in an aqueous solution for disinfection containing a percarboxylic acid as an active ingredient is a concentration effective for sterilization or disinfection (equal to or greater than the threshold).

"Threshold" as used herein means the boundary between the effective concentration (effective microbicidal concentration) at which the percarboxylic acid contained in an aqueous solution for disinfection exhibits a sterilization, microbicidal, or disinfection effect and the ineffective concentration (ineffective microbicidal concentration) at which the percarboxylic acid does not exhibit the effect; i.e., it means the critical point (minimum effective microbicidal concentration: mass %). That is, when an aqueous solution for disinfection contains a percarboxylic acid at a concentration equal to or greater than the threshold, the aqueous solution for disinfection effectively exhibits a sterilization, microbicidal, or disinfection effect. When an aqueous solution for disinfection contains a percarboxylic acid at a concentration less than the threshold, the aqueous solution for disinfection cannot exhibit the desired sterilization, microbicidal, or disinfection effect. The threshold varies depending on the type of percarboxylic acid contained in an aqueous solution for disinfection, the type and use of a test sample for sterilization, microbicide, or disinfection, and the type of microorganisms to be killed, and can be suitably set according to these. The threshold (minimum effective microbicidal concentration) of the percarboxylic acid can be set within the range of, for example, 0.01 to 1 mass %, preferably 0.03 to 0.5 mass %, and more preferably 0.05 to 0.4 mass %. An aqueous solution for disinfection containing a percarboxylic acid at a concentration equal to or greater than the threshold set means that the aqueous solution for disinfection contains the percarboxylic acid at an effective microbicidal concentration and exhibits the desired sterilization, microbicidal, or disinfection effect.

The device may be any device as long as it comprises a substrate comprising at least a part capable of the determination described above (determination part). The determination part can be impregnated with the indicator solution of the present invention and then dried so that the determination part comprises a member that is capable of retaining (supporting or holding) at least (a) the starch, (b) the iodide, and (c) the thiosulfate of the indicator solution in a dry state. The determination part of the device of the present invention, which comprises a member retaining (supporting or holding) (a) the starch, (b) the iodide, and (c) the thiosulfate in a dry state, is used in such a manner that it is immersed in an aqueous solution for disinfection containing a percarboxylic acid to be measured. When the determination part is immersed in the aqueous solution for disinfection, it comes into contact with the percarboxylic acid in the aqueous solution for disinfection to cause an iodine-starch reaction, thereby exhibiting a predetermined color. The determination part is thus a determination part for the concentration of percarboxylic acid as well as a reaction part (reaction area) for an iodine-starch reaction in the device of the present invention. In this sense, the determination part can also be said to be a "reaction and determination part." Therefore, the term "determination part" used in the present specification is intended to include the meaning of "reaction and determination part."

The device of the present invention need not have any particular shape as long as it comprises at least a determination part comprising the member described above. The device of the present invention may have the form of, simply, a strip or stick (test strip). The device may be placed in a container before use. The device may be placed in a container in a state in which it is folded into a roll shape or a bellows shape.

The material of the member is not limited as long as it can retain (support or hold) at least (a) the starch, (b) the iodide, and (c) the thiosulfate after impregnation with the indicator solution described above and drying. For example, paper, nonwoven fabric, a porous polymer sheet, etc. can be used. The paper preferably has good water-absorbing properties. Examples include, but are not limited to, filter paper No. 5C for quantitative analysis (Advantec Toyo Kaisha, Ltd.). The nonwoven fabric may be a material used for filters. Examples include, but are not limited to, polypropylene nonwoven fabric Splitop SP (Nippon Non-woven Fabrics Co., Ltd.). Examples of the porous polymer sheet include, but are not limited to, a mixed cellulose ester membrane filter (Merck Millipore), which is commercially available for filtration.

The size of the determination part of the device of the present invention, which comprises the above member, is not limited. When the device is in the form of, for example, a strip or stick and the determination part is disposed at the tip of a holding part as described later, the determination part is, for example, about 0.01 to 1 mm thick, about 2 to 20 mm long, and about 2 to 20 mm wide.

As described above, the determination part is impregnated with the indicator solution of the present invention and then dried. The determination part thereby contains at least (a) the starch, (b) the iodide, and (c) the thiosulfate of the indicator solution in a dry state. The manner in which (a) the starch, (b) the iodide, and (c) the thiosulfate are present in the determination part is not particularly limited as long as the effects of the present invention are attained.

The amounts of the components per unit area (1 cm$^2$) of the determination part are not particularly limited as long as the effects of the present invention are attained. The total amount (dry weight) of (a) the starch, (b) the iodide, and (c) the thiosulfate per unit area (1 cm$^2$) of the determination part is preferably greater than 0.24 mg (0.24 mg/cm$^2$) in order for the determination part to react with a percarboxylic acid contained at a concentration equal to or greater than the threshold in an aqueous solution for disinfection to thereby exhibit clear black. The total amount (dry weight) of (a) the starch, (b) the iodide, and (c) the thiosulfate per unit area (1 cm$^2$) of the determination part is preferably 0.25 mg/cm$^2$ or more, more preferably 0.28 mg/cm$^2$ or more, and even more preferably 0.30 mg/cm$^2$ or more. The upper limit is not particularly limited and is, for example, 8 mg/cm$^2$ or less, and preferably 5 mg/cm$^2$ or less.

The amount (dry weight) of (b) the iodide per unit area (1 cm$^2$) of the determination part is not limited and is 0.035 mg/cm$^2$ or more, preferably 0.05 mg/cm$^2$ or more, and more preferably 0.15 mg/cm$^2$ or more. The upper limit is not particularly limited and is, for example, 1 mg/cm$^2$ or less, and preferably 0.85 mg/cm$^2$ or less. The amount of (c) the thiosulfate per unit area (1 cm$^2$) of the determination part is 0.04 mg/cm$^2$ or more, preferably 0.05 mg/cm$^2$ or more, and more preferably 0.15 mg/cm$^2$ or more. The upper limit is not particularly limited and is, for example, 1.5 mg/cm$^2$ or less, and preferably 1 mg/cm$^2$ or less.

Among (a) the starch, (b) the iodide, and (c) the thiosulfate contained in the indicator solution of the present invention, the amount of (b) the iodide contained per unit area (1 cm$^2$) of the determination part can be set according to the following formula on the basis of the threshold (mass %) of the effective concentration of percarboxylic acid in an aqueous solution for disinfection to be measured.

$$A/B<2.5$$

A: the threshold (mass %) of the effective concentration of percarboxylic acid contained in an aqueous solution for disinfection to be measured
B: the dry weight (mg/cm$^2$) of iodide ion contained in the determination part of the PCAC-determining device A/B may be any value that satisfies the above value. It is desirable that the amount of (b) the iodide held at the determination part is adjusted so that A/B is preferably within the range of 0.2 to less than 2.5, more preferably 0.5 to 2.3, and even more preferably 0.7 to 2.3.

Similarly, the amount of (c) the thiosulfate per unit area (1 cm$^2$) of the reaction and determination part can be set according to the following formula on the basis of the threshold (mass %) of the effective concentration of percarboxylic acid in an aqueous solution for disinfection to be measured.

$$A/C<2.0$$

A: the threshold (mass %) of the effective concentration of percarboxylic acid contained in an aqueous solution for disinfection to be measured
C: the dry weight (mg/cm$^2$) of thiosulfate ion contained in the determination part of the PCAC-determining device A/C may be any value that satisfies the above value. It is desirable that the amount of (c) the thiosulfate held at the determination part is adjusted so that A/C is preferably within the range of 0.3 to 1.8, more preferably 0.5 to 1.5, and even more preferably 0.7 to 1.5.

The device of the present invention may further comprise a part for improving handling or convenience when used, in addition to the part described above. The device of the present invention is used in such a manner that a user (a person who makes determination) picks up the device, immerses the determination part in an aqueous solution for disinfection containing a percarboxylic acid, and visually determines whether the concentration of percarboxylic acid is equal to or greater than the threshold (whether the concentration of percarboxylic acid is an effective microbicidal concentration), on the bases of the color exhibited at the part, as described later. Thus, the device preferably comprises a holding part for allowing the user to hold the device, in addition to the determination part. The holding part may be formed from a substrate made of the same material as that of the determination part; however, the holding part may be formed from a substrate made of a different material because the holding part need not be impregnated with the indicator solution of the present invention. The substrate is not limited and is, for example, a plastic sheet. The size of the holding part is not particularly limited. When the device of the present invention is in the form of, for example, a strip or stick as described above and the determination part is disposed at an end of the holding part, the holding part is, for example, about 0.1 to 5 mm thick, about 50 to 100 mm long, and about 2 to 20 mm wide, although there is no limitation.

The device of the present invention can be provided in the form of a kit. Examples of the form of the kit include a form in which multiple strip-shaped or stick-shaped devices comprising a determination part that retains the indicator solution of the present invention in a dry state are placed in an airtight container. As described above, the device may be placed in a container in a state in which the device is folded into a roll shape or a bellows shape. In this case, the device can be cut into strips or sticks before use, and then used. The kit may comprise instructions that describe the use of the device of the present invention and/or the method for determining the concentration of percarboxylic acid in an aqueous solution for disinfection and criteria for the determination (criteria for the determination for the effective microbicidal concentration and the ineffective microbicidal concentration).

The percarboxylic acid, which is the target of the device of the present invention, is preferably a peroxide of a $C_{1-8}$ organic carboxylic acid represented by the following formula:

wherein R is hydrogen or a group represented by $CH_3(CH_2)_n$ (n=0 to 6).

Specific examples of the percarboxylic acid include peroxycarboxylic acids, such as performic acid, peracetic acid, perpropionic acid, perbutanoic acid, perpentanoic acid, perhexanoic acid, perheptanoic acid, peroctanoic acid, and the like. Performic acid, peracetic acid, and perpropionic acid are preferable, and peracetic acid is more preferable.

The device of the present invention is used as an auxiliary device for determining whether an aqueous solution for disinfection containing such a percarboxylic acid as described above as an active ingredient contains the percarboxylic acid at a concentration effective for chemical sterilization or disinfection (equal to or greater than the threshold), by immersing the device in the aqueous solution for disinfection and observing the color exhibited at the determination part. In this case, when the determination part of the device exhibits black, it can be determined that the aqueous solution for disinfection contains the percarboxylic acid at a concentration effective for chemical sterilization or disinfection (equal to or greater than the threshold) (determined to be effective). When the determination part of the device exhibits incomplete coloration (for example, black is not exhibited, or there is uneven color development (e.g., even if a black color is exhibited, whitish spots appear)), it can be determined that the aqueous solution for disinfection does not contain the percarboxylic acid at a concentration effective for chemical sterilization or disinfection (less than the threshold), and that its efficacy of chemical sterilization or disinfection is ineffective (determined to be ineffective).

Although there is no limitation, the determination may be performed by immersing the determination part of the device in an aqueous solution for disinfection at an ordinary temperature (immersion step), taking out the determination part of the device and standing the determination part of the device upright sideways on a water-absorbent tissue or the like to remove excess solution at the determination part (liquid removal step), and visually determining the degree of the color exhibited at the determination part. The immersion is generally performed for about 0.1 to 15 seconds, preferably about 1 to 10 seconds, and more preferably about 2 to 5 seconds, although there is no limitation. The liquid removal is generally performed for 1 to 10 seconds, preferably 1 to 5 seconds, and more preferably 2 to 3 seconds in a state in which the determination part is stood upright sideways on water-absorbent paper or the like. It is desirable to provide time between the liquid removal and the determination until the color development settles, preferably 1 to 60 seconds, and more preferably 3 to 10 seconds. This allows accurate determination.

The aqueous solution for disinfection for which the effective concentration can be determined using the device of the present invention contains a percarboxylic acid as an ingredient for sterilization or disinfection, as described above. The concentration range of percarboxylic acid in the aqueous solution for disinfection, which is the target of the device of the present invention, is not limited. The percarboxylic acid concentration in the aqueous solution for disinfection is, for example, within the range of 0.01 to 1 mass % (100 to 10000 ppm), preferably 0.03 to 0.5 mass % (300 to 5000 ppm), and more preferably 0.05 to 0.4 mass % (500 to 4000 ppm). That is, the determining device of the present invention can be used for an aqueous solution for disinfection containing a percarboxylic acid in the above concentration range as an active ingredient, and can be used for determining, depending on the specific use, whether the concentration of percarboxylic acid contained in the solution is a concentration effective for chemical sterilization or disinfection (effective microbicidal concentration), i.e., whether the concentration of percarboxylic acid is equal to or greater than the threshold. It is only necessary that the aqueous solution for disinfection contains a percarboxylic acid as an active ingredient for chemical sterilization or disinfection; however, the aqueous solution for disinfection may also contain one or two or more additives in addition to the component. Examples of additives include corrosion inhibitors, solubilizing agents, pH adjusters, sequestering agents, stabilizing agents, surfactants, anti-redeposition agents, and the like.

In an aqueous solution for disinfection, the effective concentration (equal to or greater than the threshold) of percarboxylic acid that exhibits an effect for chemical sterilization or disinfection varies depending on the type of percarboxylic acid and the type of microorganisms etc. to be killed, and is generally 0.01 mM or more, and preferably 0.03 mM or more. The effective concentration (equal to or greater than the threshold) can also be determined by measuring microbicidal activity at various concentrations of percarboxylic acid used depending on the type of microorganisms etc. to be killed. For example, when the percarboxylic acid is peracetic acid and target microorganisms are general bacteria, fungi, viruses, acid-fast bacteria, and spores, the effective concentration (equal to or greater than the threshold) of peracetic acid that exhibits an effect for chemical sterilization or disinfection in the aqueous solution for disinfection is preferably 0.01 mass % (100 ppm) or more, more preferably 0.03 mass % (300 ppm) or more, and particularly preferably 0.1 mass % (1000 ppm) or more.

Examples of general bacteria include, but are not limited to, *Staphylococcus aureus, Staphylococcus epidermidis, Staphylococcus hominis*, and like bacteria belonging to the genus *Staphylococcus, Enterococcus faecalis, Enterobacter cloacae, Escherichia coli, Pseudomonas aeruginosa, Burkholderia cepacia, Serratia marcescens, Protis vulgaris, Klebsiella pneumoniae, Salmonella typhi*, MRSA, and the like. The effective concentration (equal to or greater than the threshold) of peracetic acid that exhibits an effect for chemical sterilization or disinfection on these general bacteria is preferably 0.01 mass % or more.

Examples of fungi include, but are not limited to, *Aspergillus niger, Candida albicans, Filobasidiella neoformans, Trichophyton mentagrophytes*, and the like. The effective concentration (equal to or greater than the threshold) of peracetic acid that exhibits an effect for chemical sterilization or disinfection on these fungi is preferably 0.01 mass % or more, more preferably 0.03 mass % or more, and particularly preferably 0.05 mass % or more.

Examples of viruses include, but are not limited to, viruses that have envelopes, such as adenovirus and herpes simplex virus; viruses that do not have envelopes, such as norovirus and poliovirus; and the like. The effective concentration (equal to or greater than the threshold) of peracetic acid that exhibits an effect for chemical sterilization or disinfection on these viruses is preferably 0.01 mass % or more, more preferably 0.03 mass % or more, and particularly preferably 0.05 mass % or more.

Examples of acid-fast bacteria include, but are not limited to, *Mycobacterium tuberculosis, M. avium, M. intracellulare, M. terrae, M. kansasii*, and the like. The effective concentration (equal to or greater than the threshold) of peracetic acid that exhibits an effect for chemical sterilization or disinfection on these acid-fast bacteria is preferably 0.01 mass % or more, more preferably 0.03 mass % or more, and particularly preferably 0.05 mass % or more.

Examples of spores include, but are not limited to, *Bacillus subtilis* (spore form), *Bacillus cereus* (spore form), *Clostridium sporogenes* (spore form), *Clostridium difficile* (spore form), and the like. The effective concentration (equal to or greater than the threshold) of peracetic acid that exhibits an effect for chemical sterilization or disinfection on these spores is preferably 0.01 mass % or more, more preferably 0.03 mass % or more, and particularly preferably 0.05 mass % or more.

For disinfection of sewage etc., a percarboxylic acid may be used at a concentration of a low mass % (a low ppm) level. When a percarboxylic acid is used at a concentration lower than 0.01 mass % (100 ppm), it is necessary to perform treatment for a long period of time in order to obtain an effective disinfection effect. The proportion of percarboxylic acid used for disinfection of sewage etc. is preferably 0.001 mM or more, and more preferably 0.01 mM; when peracetic acid is used as a percarboxylic acid, the proportion of peracetic acid is, for example, 0.001 mass % (10 ppm) or more, preferably 0.03 mass % (300 ppm), and even more preferably 0.1 mass % (1000 ppm) or more.

The term "disinfection" used in the present specification includes the meanings of "cleaning," "antimicrobial," etc. The use of an aqueous solution for chemical sterilization or disinfection is not particularly limited. The aqueous solution can be used for disinfection for a liquid (liquid material) or a solid (solid material), as well as disinfection for a contaminated gas phase. The aqueous solution is preferably used for sterilization or disinfection for a solid. In the case of medical devices, such as endoscopes, a medical device is generally immersed in an aqueous solution for disinfection to bring it into contact with the aqueous solution for disinfection, thereby performing sterilization or disinfection. Such an aqueous solution for disinfection can be used repeatedly; however, the concentration of percarboxylic acid decreases with multiple uses or over time. Thus, checking before use whether the concentration of percarboxylic acid in an aqueous solution for disinfection is a concentration effective for chemical sterilization or disinfection, by using the device of the present invention enables the aqueous solution for disinfection to be used effectively and economically.

(III) Method for Determining Concentration of Percarboxylic Acid

Whether an aqueous solution for disinfection containing a percarboxylic acid as an active ingredient for chemical sterilization or disinfection contains the percarboxylic acid at a concentration effective for sterilization or disinfection (equal to or greater than the threshold), can be determined by, for example, performing the following steps (1) and (2):

(1) immersing at least the determination part of the device of the present invention in the aqueous solution for disinfection; and (2) observing color development at the determination part.

Further, the following determination step may be performed after the observation:

(3) determining that the concentration of percarboxylic acid in the aqueous solution for disinfection is effective (equal to or greater than the threshold) or ineffective (less than the threshold) for sterilization or disinfection, using the state of the color development at the determination part as an index.

When the determination part exhibits incomplete coloration (for example, black is not exhibited, or there is uneven color development (e.g., even if a black color is exhibited, whitish spots appear)), it can be determined that the aqueous solution for disinfection does not contain the percarboxylic acid at a concentration effective for chemical sterilization or disinfection (equal to or greater than the threshold), and that its microbicidal efficacy is ineffective (determined to be ineffective). When the determination part exhibits black over the part and does not exhibit incomplete coloration such as that described above, it can be determined that the aqueous solution for disinfection contains the percarboxylic acid at a concentration effective for chemical sterilization or disinfection, and that its microbicidal efficacy is effective (determined to be effective).

EXAMPLES

Experimental Examples and Examples are given below to illustrate the present invention in more detail; however, the present invention is not limited to these Experimental Examples and Examples. The following Experimental Examples were performed at ordinary pressure (atmospheric pressure) and an ordinary temperature (25±5° C.), unless otherwise stated.

Experimental Example 1

0.78 g of starch, 0.53 g of potassium iodide, and 1.0 g of sodium thiosulfate pentahydrate were dissolved in 80 g of purified water, and 20 g of ethanol was added, thereby obtaining an indicator solution. Table 1 shows the proportion (mass %) of each component in the indicator solution.

TABLE 1

|  | (mass %) Example 1 |
|---|---|
| (a) Starch | 0.76 wt % |
| (b) Potassium iodide | 0.52 wt % |
| (c) Sodium thiosulfate pentahydrate | 0.98 wt % |
| (d) Ethanol | 19.55 wt % |
| (e) Purified water | Balance |
| Total | 100.0 wt % |
| (a) + (b) + (c) | 2.26 wt % |
| Amount (dry weight) of (a) + (b) + (c) contained in determination part of test strip | 0.89 mg/cm$^2$ |

Filter paper (Whatman(registered trademark) FilterPaper 54) was impregnated with the indicator solution by immersing it in the solution, followed by drying. This was repeated twice, and the total amount (dry weight) of the starch, the potassium iodide, and the sodium thiosulfate contained per unit area (1 cm$^2$) of the filter paper was adjusted so that it was 0.89 mg/cm$^2$ as shown in Table 1. The filter paper thus prepared was cut into a 6 mm×6 mm square piece. The piece was used as a determination part and fixed at the tip of PET film cut into a 80 mm×6 mm rectangle, with double-sided adhesive tape. The following experiment was performed using this as a test strip (Example 1).

Specifically, the determination part of the test strip (Example 1) was immersed in separately prepared aqueous peracetic acid solutions of known concentrations (1900 ppm, 2100 ppm) for 3 seconds. Subsequently, an edge of the determination part of the test strip (an edge of the filter paper portion) was placed on a water-absorbent tissue (within 3 seconds) to remove excess aqueous peracetic acid solution. After 7 seconds, the state of color change at the determination part was checked (immersion: 3 seconds; liquid removal: 3 seconds; determination 7 seconds after liquid removal (10 seconds after taking out the determination part from the aqueous peracetic acid solution)). Ten people visually performed determination. The case in which the determination part was colored black was regarded as "o: positive," and the case in which the color was white or there was at least one whitish spot was regarded as "x: negative." Table 2 shows the results. The determination part of the test strip (Example 1) turned uniform black as a result of immersion in the aqueous peracetic acid solution having a peracetic acid concentration of 2100 ppm, and ten out of the ten people determined that it was positive (O). In contrast, white spots clearly appeared in a black color at the determination part as a result of immersion in the aqueous peracetic acid solution having a peracetic acid concentration of 1900 ppm, and ten out of the ten people determined that it was negative (x).

As a comparative experiment, a test strip (commercial available product A) for determining the concentration of a peracetic acid preparation using an iodine-starch reaction (Comparative Example 1) was immersed in an aqueous peracetic acid solution having the same peracetic acid concentration as each of those described above (1900 ppm, 2100 ppm), and the ten people visually performed determination in the same manner. The test strip (commercial available product A) is characterized in that the test strip is colored bluish purple when reacting with a predetermined concentration of peracetic acid. Since the reaction does not occur at both end portions of the determination part of the test strip (commercial available product A), the case in which the reaction area excluding both the ends was colored dark blue was regarded as "0: positive," and the case in which a white portion appeared in dark blue was regarded as "x: negative." Table 2 shows the results.

TABLE 2

Comparison of Example 1 with commercially available product A

|  | Example 1 | | Comparative Example 1 (commercially available product A) | |
|---|---|---|---|---|
|  | 1900 ppm | 2100 ppm | 1900 ppm | 2100 ppm |
| Person 1 | x | o | x | x |
| Person 2 | x | o | x | x |
| Person 3 | x | o | x | o |
| Person 4 | x | o | x | o |
| Person 5 | x | o | x | o |
| Person 6 | x | o | o | o |
| Person 7 | x | o | o | o |
| Person 8 | x | o | x | o |
| Person 9 | x | o | x | o |
| Person 10 | x | o | x | x |
| A/B |  | 1.35 | — |  |
| A/C |  | 1.21 | — |  | x: negative;
o: positive;
—: Not calculable
A: the threshold (0.21 wt %) of the effective concentration of peracetic acid contained in an aqueous peracetic acid solution
B: the dry weight (mg/cm$^2$) of iodide ion held per unit area (1 cm$^2$) of the determination part of a test strip (Example 1: 0.155)
C: the dry weight (mg/cm$^2$) of thiosulfate ion held per unit area (1 cm$^2$) of the determination part of a test strip (Example 1: 0.174)

The ten people were of the opinion that in commercial available product A (Comparative Example 1), the white spot in the dark blue that appeared after the reaction was less noticeable, and that it was thus difficult to perform determination. Actually, as shown in Table 2, five people, which corresponds to half of the group, could not distinguish the aqueous peracetic acid solution having a peracetic acid concentration of 2100 ppm from the aqueous peracetic acid solution having a peracetic acid concentration of 1900 ppm with commercial available product A (Comparative Example 1).

An iodine-starch reaction is generally a reaction in which iodine molecules enter the three-dimensional structure of starch, and bluish purple is exhibited. However, when the test strip of Example 1 was used, a bluish color was not observed, and the determination part was colored clear black. As a result, the contrast between black and white became clear, and when the reaction was insufficient, white spots occurring in black were exhibited more clearly. The test strip of Example 1 thus makes it easier to distinguish between positive and negative (effective and ineffective) and enables accurate determination.

Experimental Example 2

Indicator solutions (Examples 2 to 4 and Comparative Example 2) having ethanol concentrations that are different from that of the indicator solution prepared in Experimental Example 1 were prepared. Table 3 (A) shows the composition of each solution. Test strips having a determination part were prepared using these indicator solutions in the same manner as in Experimental Example 1. The determination part of each test strip was immersed in aqueous peracetic acid solutions at various concentrations, and color development was checked, in the same manner as in Experimental Example 1. Table 3 (B) shows the results.

TABLE 3

|  | Example | | | Comparative Example (mass %) |
|---|---|---|---|---|
|  | 2 | 3 | 4 | 2 |
| (A) Composition of indicator solution used for preparing test strip | | | | |
| Component | | | | |
| (a) Soluble starch | 0.80 | 0.78 | 0.78 | 0.78 |
| (b) Potassium iodide | 0.54 | 0.53 | 0.53 | 0.53 |
| (c) Sodium thiosulfate pentahydrate | 1.03 | 1.46 | 1.46 | 1.46 |
| (d) Ethanol | 20.56 | 29.17 | 19.45 | 0.0 |
| (e) Purified water | Balance | Balance | Balance | Balance |
| Total | 100.00 | 100.00 | 100.00 | 100.00 |
| (a) + (b) + (c) | 2.37 | 2.77 | 2.77 | 2.77 |
| Amount (dry weight: mg/cm$^2$) of (a) + (b) + (c) contained in determination part of test strip | 0.888 | 1.037 | 1.037 | 1.037 |
| (B) Color exhibited when a test strip was reacted with aqueous peracetic acid solutions at various concentrations | | | | |
| Concentration of peracetic acid | | | | |
| 1500 ppm | x | — | — | ▲ |
| 1800 ppm | x | — | — | ▲ |
| 2000 ppm | ○ | ○ | ○ | ● |
| 3200 ppm | ○ | — | — | ● |
| A/B | 1.29 | 1.32 | 1.32 | — |
| A/C | 1.15 | 0.81 | 0.81 | — |

A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip
Criteria for determination of color
○: Uniform black = positive
x: Mottled black and white = negative
●: Brownish dark blue
▲: Mottled dark blue, brown, and pale color
■: Brown
—: Determination was not carried out.

As shown in Table 3(B), when the determination part of the test strip (Example 2) prepared using the indicator solution containing ethanol in an amount of about 20.6 mass % was immersed in an aqueous peracetic acid solution having a peracetic acid concentration of 2000 ppm or more, the determination part became uniform black. When the peracetic acid concentration in an aqueous peracetic acid solution was 1800 ppm or less, a white portion appeared in black. This shows that according to the test strip (Example 2), the case in which the peracetic acid concentration in an aqueous peracetic acid solution is 2000 ppm or more can be regarded as effective, and the case in which the peracetic acid concentration in an aqueous peracetic acid solution is 1800 ppm or less can be regarded as ineffective. That is, the above results show that by using the test strip (Example 2), distinction between effective and ineffective can be made with a peracetic acid concentration difference of only 200 ppm (=0.02%). The test strips (Examples 3 and 4) respectively prepared using the indicator solutions containing ethanol in an amount of about 29.2 mass % and an amount of about 19.5 mass % became uniform black when the peracetic acid concentration was 2000 ppm, as in Example 2 (distinguishable effective microbicidal concentration was 2000 ppm).

In contrast, the test strip (Comparative Example 2) turned brownish dark blue when the peracetic acid concentration was 2000 ppm or more, and exhibited a mottled pattern of dark blue, brown, and a pale color when the peracetic acid concentration was 1800 ppm or less; however, distinction between negative and positive could not be clearly made. The test strip of Comparative Example 2 was prepared using an indicator solution having the same reagent composition (components, amounts, etc.) as those in Examples 3 and 4, except that only water was used as a solvent.

These results reveal that the peracetic acid concentration in a test sample (an aqueous peracetic acid solution) can be clearly distinguished by the contrast between black and white when the test strips (Examples 2 to 4) individually prepared using the indicator solutions containing ethanol in appropriate amounts in addition to water were used; whereas, the test strip (Comparative Example 2) prepared using the indicator solution free of ethanol exhibited a mixed color of dark blue and brown even when reacting with peracetic acid, which makes it difficult to distinguish the peracetic acid concentration in a test sample, and this is a factor that causes a determination error. Specifically, the above results show that adding a water-soluble organic solvent, such as ethanol, as a color development improvement agent to an indicator solution is useful for determining the percarboxylic acid concentration with high accuracy.

Experimental Example 3

Taking the results of Experimental Example 2 into consideration, indicator solutions in which the ethanol concentration was about 20 mass % and the proportions of the other components were varied were prepared, and test strips (Examples 5 to 10) were prepared in the same manner as in Experimental Example 1. Table 4(A) shows the composition of each indicator solution. The determination part of each test strip was immersed in aqueous peracetic acid solutions at various concentrations, and color development was checked, in the same manner as in Experimental Example 1. Table 4(B) shows the results.

TABLE 4

|  | Example | | | | | | (mass %) |
|---|---|---|---|---|---|---|---|
|  | 5 | 6 | 7 | 8 | 9 | 10 | |
| (A) Composition of indicator solution used for preparing test strip | | | | | | | |
| Component | | | | | | | |
| (a) Soluble starch | 0.77 | 0.86 | 0.95 | 0.96 | 1.07 | 1.17 | |
| (b) Potassium iodide | 0.52 | 0.61 | 0.71 | 0.32 | 0.32 | 0.32 | |

TABLE 4-continued

|  | Example | | | | | | (mass %) |
| --- | --- | --- | --- | --- | --- | --- | --- |
|  | 5 | 6 | 7 | 8 | 9 | 10 | |
| (c) Sodium thiosulfate pentahydrate | 1.07 | 0.98 | 0.97 | 0.98 | 0.98 | 0.98 | |
| (d) Ethanol | 19.53 | 19.51 | 19.47 | 19.55 | 19.53 | 19.50 | |
| (e) Purified water | Balance | Balance | Balance | Balance | Balance | Balance | |
| Total | 100.00 | 100.00 | 100.00 | 100.00 | 100.00 | 100.00 | |
| (a) + (b) + (c) | 2.36 | 2.45 | 2.63 | 2.26 | 2.37 | 2.47 | |
| Amount (dry weight: mg/cm$^2$) of (a) + (b) + (c) contained in determination part of test strip | 0.883 | 0.916 | 0.988 | 0.845 | 0.888 | 0.924 | |
| (B) Color exhibited when a test strip was reacted with aqueous peracetic acid solutions at various concentrations | | | | | | | |
| Peracetic acid concentration | | | | | | | |
| 1900 ppm | x | x | x | x | x | x | |
| 2100 ppm | ○ | x | x | x | ○ | ○ | |
| 2200 ppm | — | ○ | ○ | ○ | — | — | |
| A/B | 1.43 | 1.26 | 1.09 | 2.39 | 2.28 | 2.28 | |
| A/C | 1.15 | 1.33 | 1.33 | 1.33 | 1.27 | 1.27 | |

A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip
Criteria for determination of color
○: Uniform black = positive
x: Mottled black and white = negative
—: Determination was not carried out.

As shown in Table 4(B), according to the test strips of Examples 5, 9, and 10, the case in which the peracetic acid concentration was 2100 ppm or more was regarded as "positive," and the case in which the peracetic acid concentration was 1900 ppm or less was regarded as "negative"; a concentration difference of only 200 ppm between them was sensitively distinguished. According to the test strips of Examples 6 to 8, the case in which the peracetic acid concentration was 2200 ppm or more was regarded as "positive," and the case in which the peracetic acid concentration was 2100 ppm or less was regarded as "negative"; a difference of only 100 ppm between them was sensitively distinguished. These results show that the desired peracetic acid concentration for determination can be freely set by adding a predetermined amount of ethanol and suitably adjusting the composition in preparing an indicator solution, and that a slight peracetic acid concentration difference of 100 to 200 ppm can be sensitively detected to make distinction between effective and ineffective with high accuracy. That is, if an indicator solution contains ethanol in a predetermined amount, by suitably adjusting the other components of the indicator solution according to the desired peracetic acid concentration for determination, a test strip (a percarboxylic acid concentration-determining device) capable of sensitively distinguishing the peracetic acid concentration in an aqueous solution for chemical sterilization or disinfection (i.e., distinguishing between the effective microbicidal concentration and the ineffective microbicidal concentration), can be prepared.

Experimental Example 4

Indicator solutions containing water in smaller amounts and the other components except for ethanol in larger amounts were prepared, and test strips (Examples 11 and 12) were prepared in the same manner as in Experimental Example 1. Table 5(A) shows the composition of each indicator solution. The determination part of each test strip was immersed in aqueous peracetic acid solutions at various concentrations, and color development was checked, in the same manner as in Experimental Example 1. Table 5(B) shows the results.

TABLE 5

|  | Example | (mass %) |
| --- | --- | --- |
|  | 11 | 12 |
| (A) Composition of indicator solution used for preparing test strip | | |
| Component | | |
| (e) Purified water | 69.69 wt % | 70.23 wt % |
| (a) Soluble starch | 4.36 wt % | 4.13 wt % |
| (b) Potassium iodide | 2.96 wt % | 2.81 wt % |
| (c) Sodium thiosulfate pentahydrate | 5.57 wt % | 5.27 wt % |
| (d) Ethanol | 17.42 wt % | 17.56 wt % |
| Total | 100.00 wt % | 100.00 wt % |
| (a) + (b) + (c) | 12.89 wt % | 12.21 wt % |
| Amount (dry weight: mg/cm$^2$) of (a) + (b) + (c) contained in determination part of test strip | 4.82 mg/cm$^2$ | 4.57 mg/cm$^2$ |

TABLE 5-continued

|  | Example (mass %) | |
| --- | --- | --- |
|  | 11 | 12 |
| (B) Color exhibited when a test strip was reacted with aqueous peracetic acid solutions at various concentrations | | |
| Peracetic acid concentration | | |
| 6600 ppm | x | x |
| 6800 ppm | ○ | ○ |
| A/B | 0.81 | 0.85 |
| A/C | 0.72 | 0.76 |

A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip
Criteria for determination of color
○: Uniform black = positive
x: Mottled black and white = negative As shown in Table 5(B), when immersed in the aqueous peracetic acid solution having a peracetic acid concentration of 6600 ppm, the test strips of Examples 11 and 12 both showed white spots in black (negative). On the other hand, when the peracetic acid concentration in an aqueous peracetic acid solution was 6800 ppm, they became uniform black (positive). These results show that according to a test strip prepared using the indicator solution of the present invention, determination can be sensitively made also for aqueous peracetic acid solutions containing a high concentration of peracetic acid even if the concentration difference is only 200 ppm.

Experimental Example 5

Indicator solutions in which the ethanol concentration was about 20 mass % and the proportions of the other components were varied were prepared, and test strips (Examples 13 to 19) were prepared in the same manner as in Experimental Example 1. Table 6(A) shows the composition of each indicator solution. The determination part of each test strip was immersed in aqueous peracetic acid solutions at various concentrations, and color development was checked, in the same manner as in Experimental Example 1. Table 6(B) shows the results.

TABLE 6

| Peracetic acid concentration | Example (mass %) | | | | | | |
| --- | --- | --- | --- | --- | --- | --- | --- |
|  | 13 | 14 | 15 | 16 | 17 | 18 | 19 |
| (A) Composition of indicator solution used for preparing test strip | | | | | | | |
| (a) Soluble starch | 0.37 | 0.23 | 0.27 | 0.31 | 0.35 | 0.39 | 0.58 |
| (b) Potassium iodide | 0.13 | 0.16 | 0.18 | 0.21 | 0.24 | 0.26 | 0.39 |
| (c) Sodium thiosulfate pentahydrate | 0.25 | 0.30 | 0.35 | 0.40 | 0.45 | 0.49 | 0.74 |
| (d) Ethanol | 19.85 | 19.86 | 19.84 | 19.81 | 19.79 | 19.78 | 19.66 |
| (e) Purified water | Balance | Balance | Balance | Balance | Balance | Balance | Balance |
| Total | 100.00 | 100.00 | 100.00 | 100.00 | 100.00 | 100.00 | 100.00 |
| (a) + (b) + (c) | 0.75 | 0.69 | 0.80 | 0.92 | 1.04 | 1.14 | 1.71 |
| Amount (dry weight: mg/cm$^2$) of (a) + (b) + (c) contained in determination part of test strip | 0.282 | 0.258 | 0.301 | 0.343 | 0.386 | 0.428 | 0.639 |
| (B) Color exhibited when a test strip was reacted with aqueous peracetic acid solutions at various concentrations | | | | | | | |
| 600 ppm | x | — | — | — | — | — | — |
| 700 ppm | — | x | — | — | — | — | — |
| 800 ppm | ○ | — | x | — | — | — | — |
| 900 ppm | — | ○ | — | x | — | — | — |
| 1000 ppm | — | — | ○ | — | x | — | — |
| 1100 ppm | — | — | — | ○ | — | — | — |
| 1200 ppm | — | — | — | — | ○ | x | x |
| 1400 ppm | — | — | — | — | — | ○ | x |
| 1600 ppm | — | — | — | — | — | ○ | ○ |
| A/B | 2.11 | 2.00 | 1.92 | 1.83 | 1.79 | 1.87 | 1.43 |
| A/C | 1.90 | 1.80 | 1.69 | 1.64 | 1.60 | 1.67 | 1.28 |

A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip
Criteria for determination of color
○: Uniform black = positive
x: Mottled black and white = negative
—: Determination was not carried out.

As shown in Table 6(B), the results show that even when the peracetic acid concentration is as low as 1600 ppm or less, the test strips of Examples 13 to 19 enable the concentration to be sensitively determined with a difference of only 200 ppm.

Experimental Example 6

Indicator solutions in which the ethanol concentration was about 20 mass % and the proportions of the other components were varied were prepared, and test strips (Comparative Examples 4 to 10) were prepared in the same manner as in Experimental Example 1. Table 7(A) shows the composition of each indicator solution. Each test strip was immersed in aqueous peracetic acid solutions at various concentrations, and color development was checked, in the same manner as in Experimental Example 1. Table 7(B) shows the results.

starch, (b) potassium iodide, and (c) sodium thiosulfate contained in the determination part of each test strip was as low as 0.6 mg/cm$^2$ or less.

Experimental Example 7

Indicator solutions were prepared using various water-soluble organic solvents, and test strips (Examples 20 to 35) were prepared according to the method described in Experimental Example 1. Specifically, indicator solutions containing potassium iodide in an amount of 0.52 wt %, soluble starch in an amount of 0.77 wt %, sodium thiosulfate pentahydrate in an amount of 0.98 wt %, and water and lower alcohol in the amounts shown in Table 8 were

TABLE 7

| | Comparative Example | | | | | | (mass %) |
|---|---|---|---|---|---|---|---|
| | 4 | 5 | 6 | 7 | 8 | 9 | 10 |
| (A) Composition of indicator solution used for preparing test strip | | | | | | | |
| (a) Soluble starch | 0.150 | 0.150 | 0.179 | 0.209 | 0.224 | 0.269 | 0.298 |
| (b) Potassium iodide | 0.027 | 0.053 | 0.053 | 0.053 | 0.080 | 0.080 | 0.105 |
| (c) Sodium thiosulfate pentahydrate | 0.050 | 0.100 | 0.100 | 0.100 | 0.149 | 0.149 | 0.199 |
| (d) Ethanol | 19.955 | 19.940 | 19.934 | 19.928 | 19.909 | 19.900 | 19.880 |
| (e) Purified water | Balance | Balance | Balance | Balance | Balance | Balance | Balance |
| Total | 100.0 | 100.0 | 100.0 | 100.0 | 100.0 | 100.0 | 100.0 |
| (a) + (b) + (c) | 0.23 | 0.30 | 0.33 | 0.36 | 0.45 | 0.50 | 0.60 |
| Amount (dry weight: mg/cm$^2$) of (a) + (b) +(c) contained in determination part of test strip | 0.085 | 0.113 | 0.124 | 0.135 | 0.170 | 0.186 | 0.225 |
| (B) Color exhibited when a test strip was reacted with aqueous peracetic acid solutions at various concentrations | | | | | | | |
| 600 ppm | ▼ | ▼ | ▼ | ▼ | ▼ | ▼ | ▼ |
| 700 ppm | ▼ | ▼ | ▼ | ▼ | ▼ | ▼ | ▼ |
| 800 ppm | ▼ | ▼ | ▼ | ▼ | ▼ | ▼ | ▼ |
| 900 ppm | ▼ | ▼ | ▼ | ▼ | ▼ | ▼ | ▼ |
| 3200 ppm | ▼ | ▼ | ▼ | ▼ | ▼ | ▼ | ▼ |
| A/B | 1.30 | 1.33 | 1.33 | 1.33 | 1.33 | 1.33 | 1.33 |
| A/C | 1.19 | 1.18 | 1.18 | 1.18 | 1.19 | 1.19 | 1.21 |

A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip
Criteria for determination of color
o: Uniform black = positive
x: Mottled black and white = negative ▼: Light blue As shown in table 7(B), the test strips turned pale blue in all of the peracetic acid concentrations tested and did not exhibit black in any of the peracetic acid concentrations tested; therefore, the concentration value of peracetic acid could not be determined using the presence or absence of white spots (mottled black and white) as an index. This is believed to be because the total amount (dry weight) of (a)

prepared, and test strips were prepared. Each test strip was immersed in an aqueous peracetic acid solution at a concentration of 0.2 mass %, and color development was checked, in the same manner as in Experimental Example 1. Moreover, as Comparative Example 11, a test strip was prepared in the same manner, using an indicator solution free of an organic solvent, and the same experiment was performed. Table 8 shows the results.

TABLE 8

|   | | Comparative Example | Example | | | | | | | |
|---|---|---|---|---|---|---|---|---|---|---|
|   | | 11 | 20 | 21 | 22 | 23 | 24 | 25 | 26 | 27 |
| (a) | Soluble starch | 0.77 | 0.77 | 0.77 | 0.77 | 0.77 | 0.77 | 0.77 | 0.77 | 0.77 |
| (b) | Potassium iodide | 0.52 | 0.52 | 0.52 | 0.52 | 0.52 | 0.52 | 0.52 | 0.52 | 0.52 |
| (c) | Sodium thiosulfate pentahydrate | 0.98 | 0.98 | 0.98 | 0.98 | 0.98 | 0.98 | 0.98 | 0.98 | 0.98 |
| (d) | Ethanol | 0 | 0.5 | 0.8 | 1 | 1.5 | 2 | 9.8 | 0 | 0 |
|   | Methanol | 0 | 0 | 0 | 0 | 0 | 0 | 0 | 0 | 0 |
|   | Isopropanol | 0 | 0 | 0 | 0 | 0 | 0 | 0 | 9.8 | 0 |
|   | Propylene glycol | 0 | 0 | 0 | 0 | 0 | 0 | 0 | 0 | 0 |
|   | Glycerol | 0 | 0 | 0 | 0 | 0 | 0 | 0 | 0 | 1 |
|   | Acetone | 0 | 0 | 0 | 0 | 0 | 0 | 0 | 0 | 0 |
|   | Acetonitrile | 0 | 0 | 0 | 0 | 0 | 0 | 0 | 0 | 0 |
| (e) | Water | Balance | Balance | Balance | Balance | Balance | Balance | Balance | Balance | Balance |
|   | Total | 100 | 100 | 100 | 100 | 100 | 100 | 100 | 100 | 100 |
|   | (a) + (b) + (c) | 2.27 | 2.27 | 2.27 | 2.27 | 2.27 | 2.27 | 2.27 | 2.27 | 2.27 |
|   | Color | Bluish purple | Black | Black | Black | Black | Black | Black | Black | Black |

|   | | Example | | | | | | | |
|---|---|---|---|---|---|---|---|---|---|
|   | | 28 | 29 | 30 | 31 | 32 | 33 | 34 | 35 |
| (a) | Soluble starch | 0.77 | 0.77 | 0.77 | 0.77 | 0.77 | 0.77 | 0.77 | 0.77 |
| (b) | Potassium iodide | 0.52 | 0.52 | 0.52 | 0.52 | 0.52 | 0.52 | 0.52 | 0.52 |
| (c) | Sodium thiosulfate pentahydrate | 0.98 | 0.98 | 0.98 | 0.98 | 0.98 | 0.98 | 0.98 | 0.98 |
| (d) | Ethanol | 0 | 0 | 0 | 0 | 0 | 0 | 0.1 | 0.1 |
|   | Methanol | 0 | 0 | 0 | 0 | 0 | 0.29 | 0 | 0 |
|   | Isopropanol | 0 | 0 | 0 | 0 | 0 | 0 | 0 | 0 |
|   | Propylene glycol | 0 | 0 | 0 | 0 | 0 | 0.39 | 0 | 0 |
|   | Glycerol | 2 | 9.8 | 39.1 | 0 | 0.49 | 0 | 0 | 0 |
|   | Acetone | 0 | 0 | 0 | 9.8 | 0.49 | 0 | 0.2 | 0 |
|   | Acetonitrile | 0 | 0 | 0 | 0 | 0 | 0.29 | 0 | 0.8 |
| (e) | Water | Balance | Balance | Balance | Balance | Balance | Balance | Balance | Balance |
|   | Total | 100 | 100 | 100 | 100 | 100 | 100 | 100 | 100 |
|   | (a) + (b) + (c) | 2.27 | 2.27 | 2.27 | 2.27 | 2.27 | 2.27 | 2.27 | 2.27 |
|   | Color | Black | Black | Black | Black | Black | Black | Black | Black |

As shown in Table 8, when the ethanol concentration in an indicator solution was 0.5 mass % or more, the determination part of the test strip reacted with an effective concentration of peracetic acid to exhibit black (Examples 20 to 25). Also when isopropanol, glycerol, or acetone was used instead of ethanol, the determination part similarly reacted with peracetic acid to exhibit black (Examples 26, 27 to 30, and 31). That is, these results show that when a water-soluble organic solvent, which is not limited to ethanol, is used, a test strip that reacts with peracetic acid to exhibit a blackish clear color can be obtained. Further, two or more water-soluble organic solvents may be used in combination (Examples 32 to 35). Use of two or more organic solvents in combination can reduce the amount of each organic solvent and their total amount. In other words, when two or more organic solvents are used in combination, the effects of the present invention can be obtained with smaller amounts of the organic solvents than when used alone.

Experimental Example 8

Figure 2:
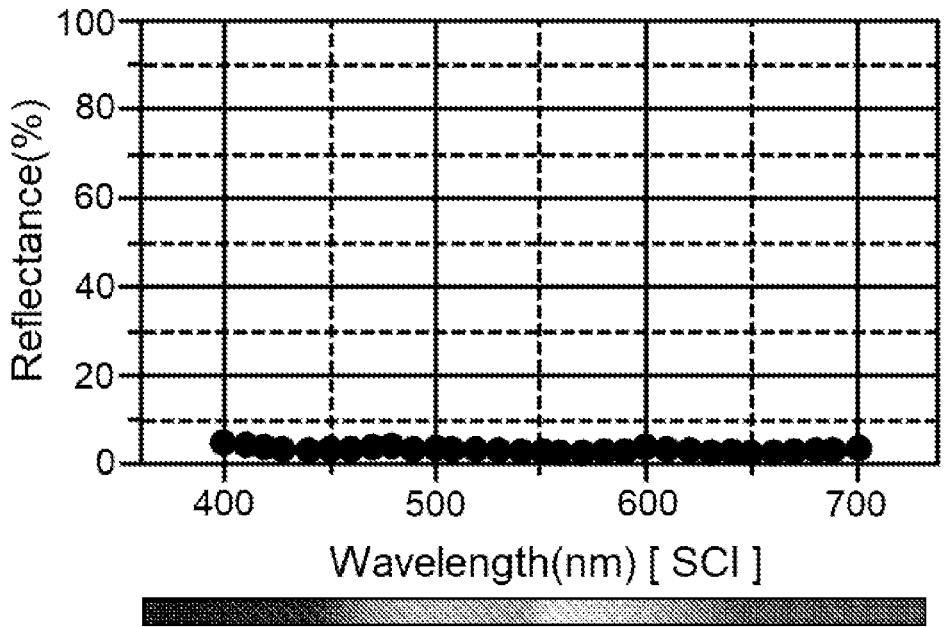
FIG. 2 shows results of reflectance (%) measured when the determination part of a test strip was irradiated with light of wavelengths of 400 to 700 nm after the part was impregnated with the indicator solution of Example 36 and dried in Experimental Example 8.
Figure 3:
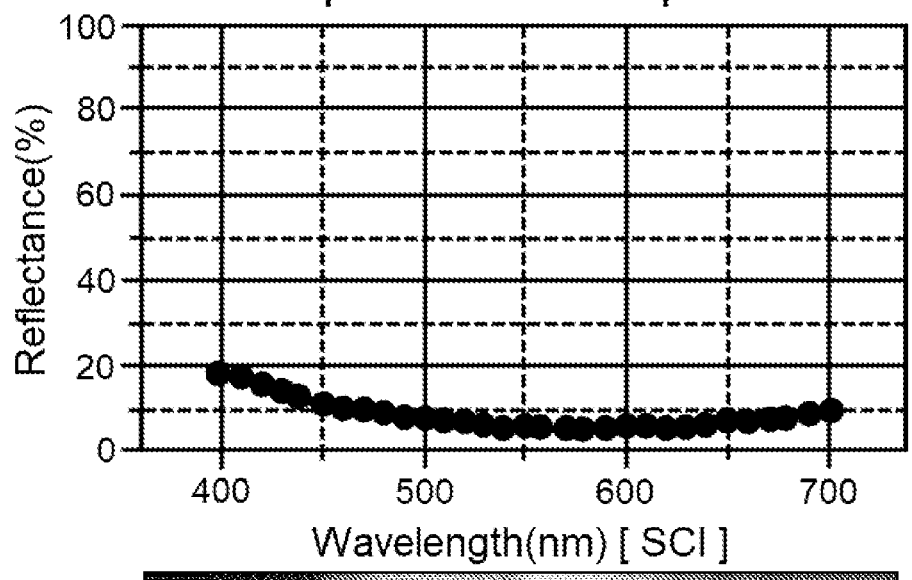
FIG. 3 shows results of reflectance (%) measured when the determination part of a test strip was irradiated with light of wavelengths of 400 to 700 nm after the part was impregnated with the indicator solution of Comparative Example 12 and dried in Experimental Example 8.
Figure 4:
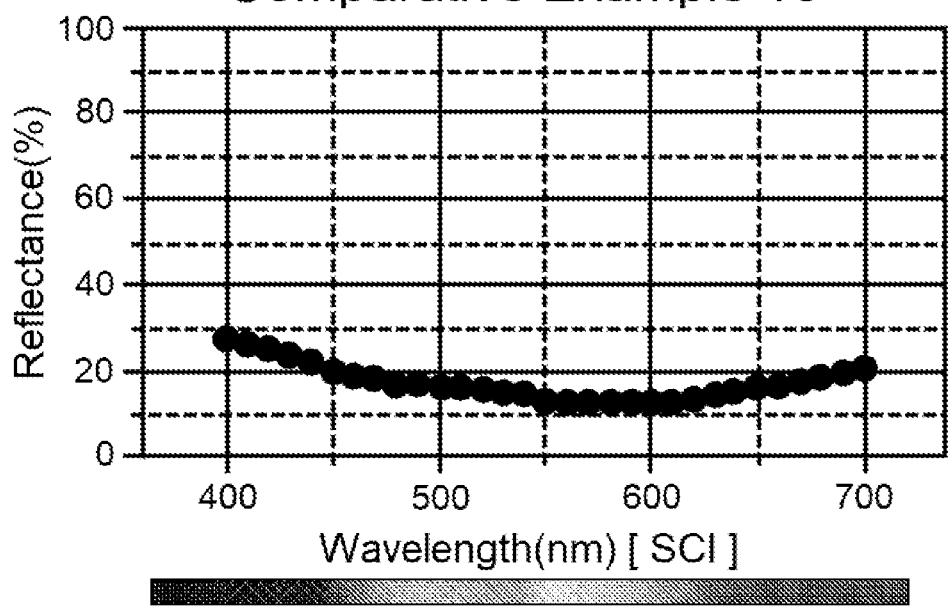
FIG. 4 shows results of reflectance (%) measured when the determination part of a test strip was irradiated with light of wavelengths of 400 to 700 nm after the part was impregnated with the indicator solution of Comparative Example 13 and dried in Experimental Example 8.

Various indicator solutions (Example 36 and Comparative Examples 12 and 13) shown in Table 9(A) were prepared. Test strips were prepared using these indicator solutions in the same manner as in Experimental Example 1. The determination part of each test strip was immersed in aqueous peracetic acid solutions at various concentrations in the same manner as in Experimental Example 1, and the color state of the determination part was evaluated by measuring $L^*a^*b^*$ values and a reflection spectrum using a spectrophotometer (Konica Minolta, Inc.; CM-600d) 7 seconds after liquid removal. Table 9(B) and FIGS. 1 to 4 show the results.

TABLE 9

(mass %)

|  | Example | Comparative Example | |
|---|---|---|---|
|  | 36 | 12 | 13 |
| (A) Composition of indicator solution used for preparing test strip | | | |
| Component | | | |
| (a) Soluble starch | 0.81 | 0.76 | 0.10 |
| (b) Potassium iodide | 0.54 | 0.52 | 0.52 |
| (c) Sodium thiosulfate pentahydrate | 1.03 | 0.97 | 0.97 |
| (d) Ethanol | 20.6 | 0.0 | 0.0 |
| (e) Purified water | Balance | Balance | Balance |
| Total | 100.0 | 100.0 | 100.0 |
| (a) + (b) + (c) | 2.38 | 2.25 | 1.59 |
| Amount (dry weight: mg/cm$^2$) of (a) + (b) + (c) contained in determination part of test strip | 0.890 | 0.842 | 0.593 |

TABLE 9-continued

| | | (mass %) | |
|---|---|---|---|
| | Example | Comparative Example | |
| | 36 | 12 | 13 |

(B) Color exhibited when a test strip was reacted with aqueous peracetic acid solutions at various concentrations

| | Filter paper only | | | |
|---|---|---|---|---|
| L | 96.56 | 18.13 | 30.06 | 44.74 |
| a | −0.25 | 1.48 | 4.76 | 2.5 |
| b | −0.09 | −4.15 | −16.93 | −13.18 |
| ΔE | | 78.56 | 68.78 | 53.52 |
| Color | White | Black | Bluish purple | Pale blue |
| A/B | | 1.29 | 1.35 | 1.35 |
| A/C | | 1.15 | 1.22 | 1.22 |

$\Delta E = (L^2 + a^2 + b^2)^{1/2}$
A: the threshold of the effective concentration of peracetic acid contained in an aqueous peracetic acid solution
B: the dry weight (mg/cm$^2$) of iodide ion contained in the determination part of a test strip
C: the dry weight (mg/cm$^2$) of thiosulfate ion contained in the determination part of a test strip As shown in Table 9(B), the determination part of the test strip of Example 36 exhibited black. In contrast, the determination parts of the test strips of Comparative Examples 12 and 13 individually prepared using the indicator solutions free of ethanol exhibited bluish purple and pale blue, respectively. Regarding the L*a*b* values, the color depth in appearance is reflected in an L value, and a difference in hue is reflected in a and b values. The greater the L, the lighter the sample. The closer to zero the a and b values are, the closer to low-saturation gray the sample is. The L value was less than 20 in Example 36, whereas the L value was greater than 30 in Comparative Examples 12 and 13. The a and b values in Example 36 were closer to 0 than those in Comparative Examples 12 and 13. That is, it was shown, not only by visual observation, but also the L*a*b* values measured using a spectrophotometer, that the test strip of Example 36 exhibited a blackish color, which has low brightness, compared with the Comparative Examples.

The reflection spectrum of Example 36 shows that the reflectance in wavelengths of 400 to 700 nm was less than 5%, which indicates that black was exhibited. In contrast, the reflection spectra of Comparative Examples 12 and 13 show that the reflectance was high near 400 nm, which indicates that a bluish color was exhibited. That is, it was shown, not only by visual observation, but also the reflection spectra measured using a spectrophotometer, that the test strip of Example 36 exhibited a blackish color compared with the Comparative Examples.

The invention claimed is:

1. An indicator solution comprising a starch, an iodide, a thiosulfate, a water-soluble organic solvent, and water, the starch, the iodide, the thiosulfate, the water-soluble organic solvent, and the water being present in the following proportions, based on the indicator solution taken as 100 mass %:
   (a) starch: 0.01 to 5 mass %;
   (b) iodide: 0.01 to 5 mass %;
   (c) thiosulfate: 0.01 to 10 mass %;
   (d) water-soluble organic solvent: 0.1 to 40 mass %; and
   (e) water: 60 to 99 mass %,
   wherein the total amount of (a), (b), and (c) is greater than 0.6 mass %.

2. The indicator solution according to claim 1, wherein (d) the water-soluble organic solvent is at least one member selected from the group consisting of $C_{1-6}$ lower alcohols, polyhydric alcohols, acetone, and acetonitrile.

3. The indicator solution according to claim 1, wherein (d) the water-soluble organic solvent is a $C_{1-6}$ lower alcohol, and the proportion of the organic solvent is 0.5 mass % or more based on the indicator solution taken as 100 mass %.

4. The indicator solution according to claim 1, for use in preparing a percarboxylic acid concentration-determining device.

5. The indicator solution according to claim 4, wherein the percarboxylic acid concentration-determining device comprises a part for determining the concentration of percarboxylic acid in an aqueous solution for chemical sterilization or disinfection (a determination part), and (a) the starch, (b) the iodide, and (c) the thiosulfate are held at the determination part in a total amount (dry weight) of greater than 0.24 mg per cm$^2$.

6. The indicator solution according to claim 5, wherein the percarboxylic acid concentration-determining device has the following characteristic:

$A/B < 2.5$ $A/C < 2.0$

A: a threshold (mass %) of an effective concentration of percarboxylic acid contained in an aqueous solution for chemical sterilization or disinfection to be measured,
B: a dry weight (mg/cm$^2$) of iodide ion contained in the determination part of the percarboxylic acid concentration-determining device,
C: a dry weight (mg/cm$^2$) of thiosulfate ion contained in the determination part of the percarboxylic acid concentration-determining device.

7. The indicator solution according to claim 4, wherein the percarboxylic acid, which is a target of the percarboxylic acid concentration-determining device, is a peroxide of a $C_{1-8}$ organic carboxylic acid.

8. A percarboxylic acid concentration-determining device comprising at least a part for determining the concentration of percarboxylic acid (a determination part), wherein a member that forms the determination part comprises the indicator solution according to claim 1 in a dry state.

9. The percarboxylic acid concentration-determining device according to claim 8, which has the following characteristics (1) to (3):
   (1) the device is for use in determining whether the concentration of percarboxylic acid in an aqueous solution for chemical sterilization or disinfection that contains a percarboxylic acid is a concentration effective for sterilization or disinfection;
   (2) the device comprises at least a part for determining the concentration of percarboxylic acid in an aqueous solution for chemical sterilization or disinfection (a determination part);
   (3) the determination part comprises (a) the starch, (b) the iodide, and (c) the thiosulfate in a total amount of greater than 0.24 mg on a dry weight basis.

10. The percarboxylic acid concentration-determining device according to claim 9, which further has the following characteristic (4):

$A/B < 2.5$ $A/C < 2.0$ (4)

A: a threshold (mass %) of an effective concentration of percarboxylic acid contained in an aqueous solution for chemical sterilization or disinfection to be measured, B: a dry weight (mg/cm$^2$) of iodide ion contained in the determination part of the percarboxylic acid concentration-determining device, C: a dry weight (mg/cm$^2$) of thiosulfate ion contained in the determination part of the percarboxylic acid concentration-determining device.

11. The percarboxylic acid concentration-determining device according to claim 9, wherein the concentration of percarboxylic acid in the aqueous solution for chemical sterilization or disinfection is 0.01 to 1 mass %.

12. The percarboxylic acid concentration-determining device according to claim 8, wherein the percarboxylic acid, which is a target in the determination, is a peroxide of a $C_{1-8}$ organic carboxylic acid.

13. A kit for determining a percarboxylic acid concentration, comprising the percarboxylic acid concentration-determining device according to claim 8.

14. A method for determining whether the concentration of percarboxylic acid in an aqueous solution for chemical sterilization or disinfection that contains a percarboxylic acid as an active ingredient is a concentration effective for chemical sterilization or disinfection, the method comprising:

allowing the aqueous solution for chemical sterilization or disinfection to come into contact with the determination part of the percarboxylic acid concentration-determining device according to claim 8 to develop a color at the determination part.

15. The method according to claim 14, comprising the following steps (1) to (3):
(1) immersing at least the determination part of the percarboxylic acid concentration-determining device in an aqueous solution for chemical sterilization or disinfection;
(2) taking out the determination part of the percarboxylic acid concentration-determining device from the aqueous solution for chemical sterilization or disinfection, and performing liquid removal; and
(3) determining effectiveness of the concentration of percarboxylic acid in the aqueous solution for chemical sterilization or disinfection, based on a state of color development at the determination part.

16. The percarboxylic acid concentration-determining device according to claim 8, wherein (d) the water-soluble organic solvent is a $C_{1-6}$ lower alcohol, and the proportion of the organic solvent is 0.5 mass % or more based on the indicator solution taken as 100 mass %.

17. The percarboxylic acid concentration-determining device according to claim 16, which has the following characteristics (1) to (3):
(1) the device is for use in determining whether the concentration of percarboxylic acid in an aqueous solution for chemical sterilization or disinfection that contains a percarboxylic acid is a concentration effective for sterilization or disinfection;
(2) the device comprises at least a part for determining the concentration of percarboxylic acid in an aqueous solution for chemical sterilization or disinfection (a determination part); and
(3) the determination part comprises (a) the starch, (b) the iodide, and (c) the thiosulfate in a total amount of greater than 0.24 mg/cm$^2$ on a dry weight basis.

18. The percarboxylic acid concentration-determining device according to claim 17, which further has the following characteristic (4):

$$A/B<2.5$$

$$A/C<2.0 \qquad (4)$$

A: a threshold (mass %) of an effective concentration of percarboxylic acid contained in an aqueous solution for chemical sterilization or disinfection to be measured, B: a dry weight (mg/cm$^2$) of iodide ion contained in the determination part of the percarboxylic acid concentration-determining device, and C: a dry weight (mg/cm$^2$) of thiosulfate ion contained in the determination part of the percarboxylic acid concentration-determining device.

19. The percarboxylic acid concentration-determining device according to claim 17, wherein the concentration of percarboxylic acid in the aqueous solution for chemical sterilization or disinfection is 0.01 to 1 mass %.

20. A kit for determining a percarboxylic acid concentration, comprising the percarboxylic acid concentration-determining device according to claim 16.

* * * * *